(12) United States Patent
Anton et al.

(10) Patent No.: US 7,495,038 B2
(45) Date of Patent: *Feb. 24, 2009

(54) MATERIALS LEADING TO IMPROVED DENTAL COMPOSITES AND DENTAL COMPOSITES MADE THEREFROM

(75) Inventors: Douglas Robert Anton, Wilmington, DE (US); Gary Delmar Jaycox, West Chester, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 342 days.

This patent is subject to a terminal disclaimer.

(21) Appl. No.: 11/431,680

(22) Filed: May 10, 2006

(65) Prior Publication Data

US 2006/0258769 A1    Nov. 16, 2006

Related U.S. Application Data

(60) Provisional application No. 60/680,763, filed on May 13, 2005.

(51) Int. Cl.
*A61K 6/083* (2006.01)

(52) U.S. Cl. ............... 523/116; 523/118; 433/228.1

(58) Field of Classification Search ............... 523/116, 523/118

See application file for complete search history.

(56) References Cited

U.S. PATENT DOCUMENTS

| 3,367,992 | A | 2/1968 | Bearden |
| 4,843,111 | A | 6/1989 | Yokoshima et al. |
| 4,883,899 | A | 11/1989 | Muramoto et al. |
| 5,159,047 | A | 10/1992 | Simms |
| 2006/0258417 | A1* | 11/2006 | Crawford et al. ............ 463/1 |
| 2006/0258771 | A1* | 11/2006 | Anton et al. ............ 523/115 |

FOREIGN PATENT DOCUMENTS

| JP | 2000-16967 | 1/2000 |
| JP | 2002-69163 | 3/2002 |

OTHER PUBLICATIONS

Kawaguchi et al, "Effect of Monomer Structure on the Mechanical Properties of Light-cured Composite Resins", Dental Materials Journal, 8 (1) : pp. 40-45, 1989.*
Kawaguchi et al, "Effect of Monomer Structure on the Mechanical Properties of Light-cured Unfilled Resins", Dental Materials Journal, 7 (2) : pp. 174-181, 1988.*

* cited by examiner

*Primary Examiner*—Tae H Yoon

(57) ABSTRACT

This invention relates to composite materials for restorative dentistry. More particularly, it relates to new components for dental composites, which impart an attractive combination of good mechanical properties and low shrinkage.

5 Claims, No Drawings

MATERIALS LEADING TO IMPROVED DENTAL COMPOSITES AND DENTAL COMPOSITES MADE THEREFROM

CROSS-REFERENCE TO RELATED APPLICATION

This application claims priority under 35 U.S.C. §109 from U.S. Provisional Application Ser. No. 60/680,763, filed May 13, 2005.

FIELD OF THE INVENTION

This invention relates to composite materials for restorative dentistry. More particularly, it relates to new components for dental composites that impart an attractive combination of good mechanical properties and low shrinkage.

BACKGROUND OF THE INVENTION

In recent years, composite materials comprising highly filled polymers have become commonly used for dental restorations. Current composite materials contain crosslinking acrylates or methacrylates, inorganic fillers such as glass or quartz, and a photoinitiator system suitable for curing by visible light. Typical methacrylate materials include 2,2'-bis [4-(2-hydroxy-3-methacryloyloxypropyl)phenyl]propane ("Bis-GMA"); ethoxylated Bisphenol A dimethacrylate ("EBPDMA"); 1,6-bis-[2-methacryloyloxyethoxycarbonylamino]-2,4,4-trimethylhexane ("UDMA"); dodecanediol dimethacrylate ("D₃MA"); and triethyleneglycol dimethacrylate ("TEGDMA"). The structural formulae for these are shown below.

Dental composite materials offer a distinct cosmetic advantage over traditional metal amalgam. However, they do not offer the longevity of amalgam in dental fillings. The primary reason for failure is excessive shrinkage during photopolymerization in the tooth cavity, which can cause leakage and bacterial reentry. Another reason is they have inadequate strength and toughness, as reflected in the measured properties of flexural strength and fracture toughness. Hence, there is still a need for new monomers and new monomer combinations which, when polymerized, impart high fracture toughness and flexural strength in the resulting composite. It is also highly desirable to have low shrinkage stress on polymerization.

One of the more common commercially used monomers is Bis-GMA. However, it is highly viscous at room temperature and difficult to work with. It is therefore diluted with a second, lower viscosity polymerizable component ("fluidizer"), a methacrylate monomer, such as TEGDMA, tetraethylene glycol dimethacrylate, or docecanediol dimethacrylate. However, while providing low viscosity, lower viscosity components (generally low molecular weight monomers) can contribute to increased shrinkage. Increasingly, Bis-GMA and TEGDMA have been combined with UDMA and EBPDMA, but shrinkage remains high enough that improvement is desirable.

A more efficient and effective fluidizing monomer that would allow dental composites to be formulated with higher proportions of the high-viscosity monomer while not compromising the mechanical properties or polymerization shrinkage of the system is a desirable invention. An effective fluidizing monomer could also allow the composite to be formulated at a higher filler level, further lowering shrinkage.

(Meth)acrylated adducts of caprolactone and tricyclodecanemethylol have been described as resinous coating mate-

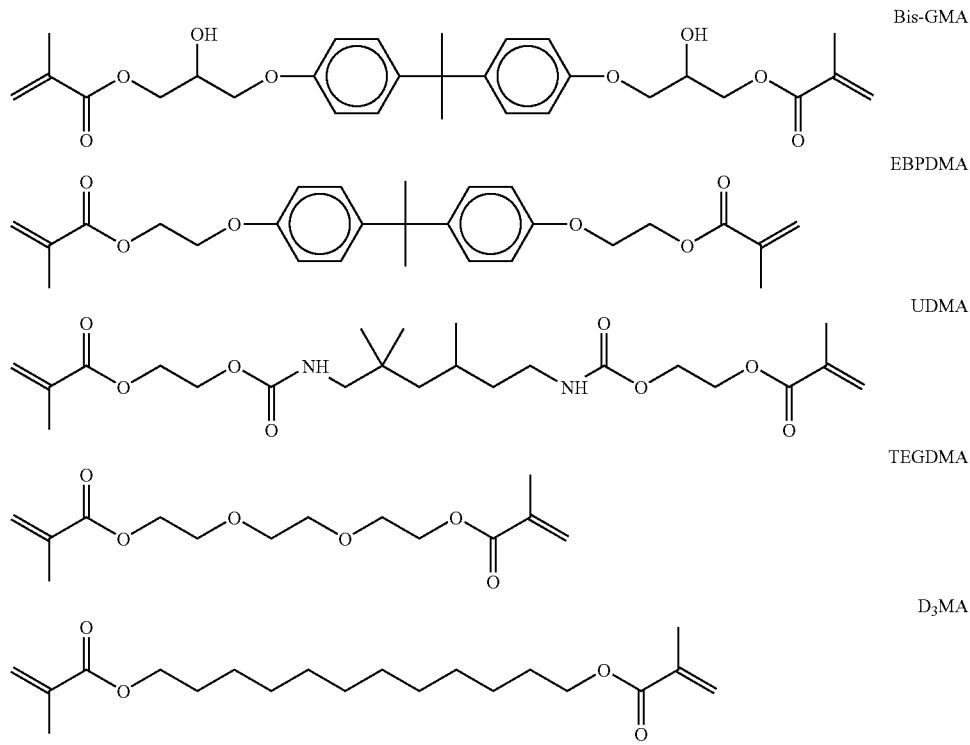

rials for optical fibers in U.S. Pat. No. 4,843,111, but not for dental composite applications.

An adduct prepared by reaction of cyclohexanedimethanol mono(meth)acrylates with lactones has been described in JP 2000016967 for coating systems, but not for dental composite applications.

Adducts prepared by reaction of cyclohexanedimethanol with caprolactone and subsequently (meth)acrylated have been described in JP2000169431 for inks, but not for dental composite applications.

Adducts of 1,4-cyclohexanedimethanol and caprolactone, not (meth)acrylated, have been described in U.S. Pat. No. 5,159,047 for coating systems, but not for dental composite applications.

A copolymer of adipic acid (erroneously translated from the Japanese as "acrylic acid" in *Chemical Abstracts* 136: 233450), ε-caprolactone, and 2-methyl-1,1-cyclohexanedimethanol has been described in JP 2002069163 as a precursor to spandex filaments, but not for dental composite applications.

There thus remains a need for efficient and effective fluidizing monomers for dental composite materials that combine reduced shrinkage with sufficiently low viscosity, high polymerization rate, and acceptable mechanical properties.

SUMMARY OF THE INVENTION

In its first aspect, the present invention is an uncured dental composite material that comprises (i) a composition comprising at least one compound having the Formula I:

$$E^1\text{-}R^1{}_n\text{—O—}R^2\text{-Q-}R^3\text{—O—}R^4{}_m\text{-}E^2 \qquad \text{I}$$

wherein:

Q is selected from the group consisting of:

(a) a carbocyclic ring containing 5 or 6 carbon atoms with up to 3 $C_{1-3}$ alkyl substituents on the ring;

(b) $S\text{-}R^5\text{-}T$ wherein S and T are each independently carbocyclic rings containing 5 or 6 carbon atoms with up to 3 $C_{1-3}$ alkyl substituents on the ring, and $R^5$ is a covalent bond or an alkylene group containing 1, 2, 3 or 4 carbon atoms; and (c) a carbocyclic fused ring system containing two fused rings containing a total of 8 to 10 carbon atoms with up to 4 $C_{1-3}$ alkyl substituents on the fused ring system;

$R^2$ and $R^3$ are each independently selected from the group consisting of a covalent bond and an alkylene group containing 1, 2, 3, or 4 carbon atoms;

$R^1$ is a repeat unit of the formula $$-\!\!\left(\!O\!-\!\left(\!\begin{array}{c}H_2\\C\end{array}\!\right)_{\!a}\!\!-\!\!\overset{O}{\underset{\|}{C}}\!\right)\!-;$$

$R^4$ is a repeat unit of the formula $$-\!\!\left(\!\overset{O}{\underset{\|}{C}}\!-\!\left(\!\begin{array}{c}H_2\\C\end{array}\!\right)_{\!a'}\!\!-\!O\!\right)\!-;$$

$E^1$ and $E^2$ are each independently $$\underset{R^6}{\overset{H_2C}{\diagdown}}\!\!\!\!\!\!\!\!\!\!\!\!\!\!\!\!\!\!\!\!\!\!\!\!\!\!\!\!\!\!\!\!\!\!\!\!\!\!\!\diagup\!\!\overset{O}{\diagdown}$$

wherein $R^6$ is H (acrylyl) or $CH_3$ (methacrylyl); and n and m are each independently an integer greater than 0;

provided that for each of the n groups of the formula $$-\!\!\left(\!O\!-\!\left(\!\begin{array}{c}H_2\\C\end{array}\!\right)_{\!a}\!\!-\!\!\overset{O}{\underset{\|}{C}}\!\right)\!-$$

a is independently an integer from 3 to 6; and provided that for each of the m groups of the formula $$-\!\!\left(\!\overset{O}{\underset{\|}{C}}\!-\!\left(\!\begin{array}{c}H_2\\C\end{array}\!\right)_{\!a'}\!\!-\!O\!\right)\!-$$

a' is independently an integer from 3 to 6;

provided that neither $R^2$ nor $R^3$ is a covalent bond bonded directly to an aromatic ring;

and provided that the degree of polymerization (dp=n+m) of the compound is between 2 and 30;

(ii) optionally at least one additional polymerizable (meth) acrylic ester;

(iii) at least one polymerization initiator compound; and (iv) at least one filler.

In its second aspect, the present invention is an uncured dental composite material incorporating at least one compound of Formula I, at least one polymerization initiator compound, at least one filler, and at least one compound of the Formula II:

wherein:
  each $R^7$ is independently hydrogen or methyl;
  each $R^8$ is an alkylene having 2 to 14 carbon atoms, or an alkenylene having 2 to 8 carbon atoms, or a divalent alicyclic hydrocarbon having 5 to 14 carbon atoms, or a phenylene, which is optionally substituted with halogen or an alkyl group having 1 to 5 carbon atoms;
  each $R^9$ is independently selected from hydrogen, acetyl, methyl, ethyl, $C_{3-6}$ linear or branched alkyl, or benzyl;
  $R^{10}$ is independently selected from hydrogen, methyl, ethyl, $C_{3-6}$ linear or branched alkyl, phenyl, or benzyl; and
  each A is a repeating unit of the formula:

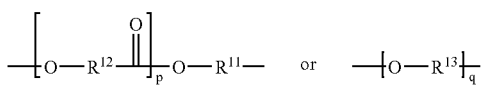

wherein:
  each $R^{11}$ is independently an alkylene having 2 or 3 carbon atoms,
  each $R^{12}$ is independently an alkylene having 2 to 7 carbon atoms,
  each $R^{13}$ is independently an alkylene having 2 to 5 carbon atoms,
  p is an integer of 1 to 10,
  and q is an integer of 1 to 10.

In its third aspect, the present invention is an uncured dental composite material incorporating at least one compound of Formula I, at least one polymerization initiator compound, at least one filler, and at least one compound of the Formula V:

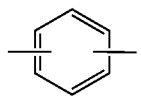

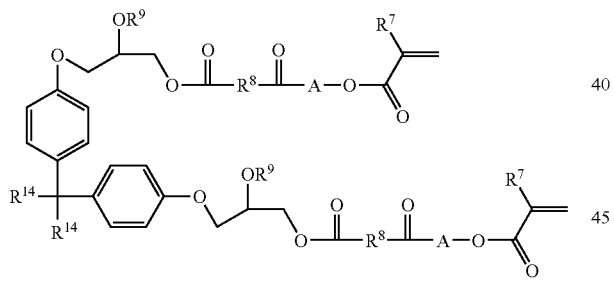

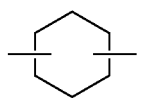

wherein $R^7$, A, $R^8$, $R^9$, are as defined in relation to the compound of Formula II, and each $R^{14}$ is independently selected from the group consisting of hydrogen, methyl, ethyl, $C_{3-6}$ linear or branched alkyl, phenyl, benzyl, and the two $R^{14}$ groups may be taken together to form a substituted or unsubstituted cyclic aliphatic ring having 5 or 6 carbons in the ring, including the carbon to which both $R^{14}$ groups are attached.

DETAILED DESCRIPTION OF THE INVENTION

In the context of this application, a number of terms are utilized.

The term "dental composite material" as used herein denotes a composition that can be used to remedy natural or induced imperfections in, or relating to, teeth. Examples of such materials are filling materials, reconstructive materials, restorative materials, crown and bridge materials, inlays, onlays, laminate veneers, dental adhesives, teeth, facings, pit and fissure sealants, cements, denture base and denture reline materials, orthodontic splint materials, and adhesives for orthodontic appliances. The term "uncured dental composite material" specifically refers to such material before it is subjected to a curing process.

As used herein, the term "alkyl" means a univalent group derived from an alkane by removing a hydrogen atom from any carbon atom: $-C_nH_{2n+1}$ where $n \geq 1$.

As used herein, the term "hydrocarbyl", when used in relation to a radical, denotes a univalent radical containing only carbon and hydrogen.

As used herein, the term "alkylene" means the divalent radical derived from an alkane by removing a hydrogen atom from each of two different carbon atoms: $-C_nH_{2n}-$ where $n \geq 1$.

As used herein, the term "alkenylene" means a straight or branched chain alkenediyl containing one olefinic bond in the chain, e.g. $-CH=CH-$ (ethenylene), $-CH_2CH=CH-$ (propenylene), etc.

As used herein, the term "carbocyclic" means having or relating to or characterized by a ring composed of carbon atoms.

As used herein, "an alicyclic group" means a non-aromatic hydrocarbon group containing a cyclic structure therein.

As used herein, the term "benzyl" refers to the $C_6H_5CH_2-$ radical.

As used herein, the term "phenyl" refers to the $C_6H_5-$ radical.

As used herein, the term "phenylene" refers to the divalent radical, $-C_6H_4-$:

As used herein, the term "cyclohexylene" refers to the divalent radical, $-C_6H_{10}-$:

As used herein, the term "carboxy methacrylate" means a compound containing a carboxylic acid and a methacrylate group.

As used herein, the terms "(meth)acrylic" and "(meth)acrylate" refer to both methacrylic and acrylic and to methacylate and acrylate, respectively.

As used herein, the terms "acrylyl" and "methacrylyl" refer to the univalent radicals

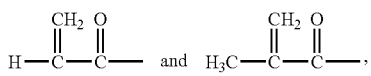

respectively.

As used herein, the term "polymerizable (meth)acrylic ester component" means one or more materials that bear (meth)acrylate groups, such that the materials are capable of undergoing free radical polymerization.

As used herein, the term "diol" means an organic compound having two hydroxyl (—OH) groups per molecule.

As used herein, the term "caprolactone" means ε-caprolactone, CAS Registry # 502-44-3:

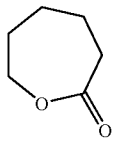

As used herein, the term "1,4,-cyclohexanedimethanol" refers to the material designated by CAS Registry # 105-08-8:

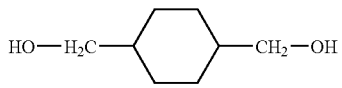

Where a range of numerical values is recited herein, unless otherwise stated, the range is intended to include the endpoints thereof, and all integers and fractions (provided the context allows) within the range.

The degree of polymerization, abbreviated dp, of a compound of Formula I is defined as the sum of the number of repeat units $R^1$ and $R^4$. The average dp for a given sample of a heterogeneous composition comprising different molecules of Formula I is defined by the average of the dp's for each molecule of Formula I in the sample.

(Meth)acrylated polyester diols

The present invention provides a dental composite material comprising a (meth)acrylated polyester diol composition containing at least one compound of the Formula I, as shown below.

$$E^1\text{-}R^1{}_n\text{—O—}R^2\text{-}Q\text{-}R^3\text{—O—}R^4{}_m\text{-}E^2 \qquad I$$

wherein:

Q is selected from the group consisting of:
 (a) a carbocyclic ring containing 5 or 6 carbon atoms with up to 3 $C_{1-3}$ alkyl substituents on the ring;
 (b) S-$R^5$-T wherein S and T are each independently carbocyclic rings containing 5 or 6 carbon atoms with up to 3 $C_{1-3}$ alkyl substituents on the ring, and $R^5$ is a covalent bond or an alkylene group containing 1, 2, 3 or 4 carbon atoms; and
 (c) a carbocyclic fused ring system containing two fused rings containing a total of 8 to 10 carbon atoms with up to 4 $C_{1-3}$ alkyl substituents on the fused ring system;

$R^2$ and $R^3$ are each independently selected from the group consisting of a covalent bond and an alkylene group containing 1, 2, 3, or 4 carbon atoms;

$R^1$ is a repeat unit of the formula

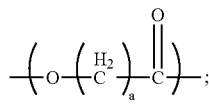

$R^4$ is a repeat unit of the formula

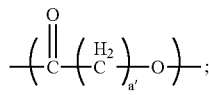

$E^1$ and $E^2$ are each independently

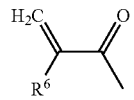

wherein $R^6$ is H (acrylyl) or $CH_3$ (methacrylyl); and n and m are each independently an integer greater than 0;

provided that for each of the n groups of the formula

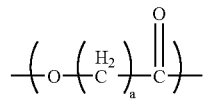

a is independently an integer from 3 to 6; and provided that for each of the m groups of the formula

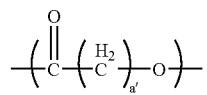

a' is independently an integer from 3 to 6;

provided that neither $R^2$ nor $R^3$ is a covalent bond bonded directly to an aromatic ring;

and provided that the degree of polymerization (dp) of the compound is between 2 and 30.

Examples of Q wherein Q is a carbocyclic ring containing 5 or 6 carbon atoms with up to 3 $C_{1-3}$ alkyl substituents on the ring include, but are not limited to:

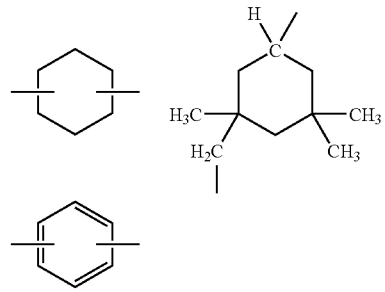

Examples of Q wherein Q is S-$R^5$-T wherein S and T are each independently carbocyclic rings containing 5 or 6 carbon atoms with up to 3 $C_{1-3}$ alkyl substituents on the ring, and $R^5$ is a covalent bond or an alkylene group containing 1, 2, 3 or 4 carbon atoms include, but are not limited to:

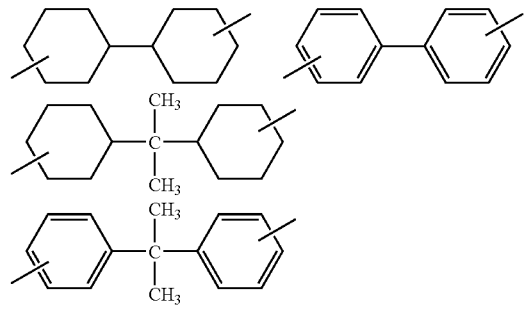

Examples of Q wherein Q is a carbocyclic fused ring system containing two fused rings containing a total of 8 to 10 carbon atoms with up to 4 $C_{1-3}$ alkyl substituents on the fused ring system include, but are not limited to:

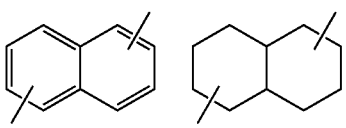

It is preferred that $R^2$ and $R^3$ are identical and that each is a covalent bond or methylene (—$CH_2$—).

In a preferred embodiment of the invention Q is a carbocyclic ring, more preferably it is cyclohexylene, most preferably 1,4-cyclohexylene.

When Q is S-$R^5$-T it is preferred that $R^5$ is 2,2-propylene or methylene. It is also preferred that S and T are each cyclohexylene, and more preferred that S and T are 1,4-cyclohexylene.

In a preferred embodiment of this invention, herein referred to as "DM-CL-CHDM,", Q is 1,4-cyclohexylene, $R^2=R^3=CH_2$, a=a'=5, $R^6$ is $CH_3$, and the dp is 2 to 6.

The present invention provides dental composite materials comprising (meth)acrylated polyester diol compounds of Formula I. These (meth)acrylated polyester diol compounds are produced by a process of (1) preparing a polyester diol, and (2) converting greater than 90%, preferably all, of the terminal hydroxyl groups of the polyester diol to (meth)acrylate groups.

The polyester diol can be produced by heating a mixture that includes (1) at least one lactone

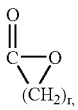

where r=a or a' as defined above;

(2) a diol, HO-$R^2$-Q-$R^3$-OH, where $R^2$, Q, and $R^3$ are defined as above; and (3) optionally a polyester polymerization catalyst (see below); and (4) optionally a solvent.

Some solvents suitable for this reaction are toluene, benzene, p-xylene, m-xylene, o-xylene, and mixtures thereof. In a preferred embodiment of this invention the reaction is run without a solvent.

Typical polyester polymerization catalysts that are useful in this reaction include, but are not limited to, dibutyl tin dilaurate, dibutyl tin diacetate, Sn(2-ethylhexanoate)$_2$, Sn(n-octanoate)$_2$; p-toluenesulfonic acid; and methanesulfonic acid. Tin(II) catalysts are preferred.

The polyester diol is then combined and optionally heated with one or more end capping agents selected from (meth) acrylic acid, (meth)acryloyl chloride, and (meth)acrylic anhydride. It is preferred that at least 90% of the diol ends be capped with a (meth)acrylate cap. The degree of capping with radically polymerizable end groups can be determined by a combination of $^1$H NMR, $^{13}$C NMR and two-dimensional NMR spectroscopy.

Some solvents for suitable for this capping reaction are tetrahydrofuran ("THF"), diethyl ether, pyridine, N,N-dimethylacetamide, N,N-dimethylformamide, dimethyl sulfoxide, N-methylpyrrolidone, $CH_2Cl_2$, $CHCl_3$, chlorobenzene, o-dichlorobenzene, benzene, toluene, xylene, and mixtures thereof. Preferably the reaction is run without a solvent.

When a solvent is not used, the reaction product is typically washed with an aqueous basic solution, such as saturated $Na_2CO_3$ (aq), to remove acidic impurities. It is then washed with water and finally with saturated NaCl solution to remove the bulk of the water. It is optionally dried with a drying agent, such as $Na_2SO_4$, to remove final traces of water.

When a solvent is used, the reaction product is typically isolated by either of two methods. The first method involves an aqueous workup. The organic phase is typically washed with an aqueous basic solution, such as saturated $Na_2CO_3$ (aq), to remove acidic impurities. It may optionally be washed with dilute aqueous acidic solution (e.g., 10% HCl) to remove basic impurities such as pyridine. Then it is washed with saturated NaCl solution to remove the bulk of the water. It is optionally dried with a drying agent, such as anhydrous $Na_2SO_4$, to remove final traces of water. Then the organic solvent is removed, optionally under vacuum, to obtain the final product. A second method for isolating the product is to perform a high vacuum distillation directly on the reaction mixture. This is typically done at 0.5 torr (66 Pa) to distill off methacrylic acid and unreacted methacrylic anhydride. The second method typically is not used when methacryloyl chloride is used as the capping agent.

It will be recognized by one skilled in the art that while the dp of individual molecules of Formula I will vary, the average degree of polymerization, dp, for a given sample of a heterogeneous composition comprising different molecules of Formula I will be determined by the original molar ratio of the lactone to the diol that was used to prepare the sample, assuming the reaction was carried to completion.

Expressed in greater detail, a preferred (meth)acrylated polyester diol can be made by a process comprising the steps of:

(a) combining caprolactone, 1,4-cyclohexanedimethanol in the molar ratio of 2:1 to 6:1, dibutyl tin dilaurate, and xylene;

(b) slowly heating the mixture to 140 C., and holding for four hours;

(c) cooling the mixture to 80° C. and filtering the product;

(d) combining the product from step (c) with methacrylic anhydride and sodium acetate;

(e) heating the mixture from step (d) to 80° C. under air for 6 hours;

(f) adding the product from step (e) to an aqueous solution of sodium carbonate with stirring for 1 hr;

(g) combining the mixture from step (f) with ethyl ether and then stirring the resulting mixture for 12 hr;

(h) separating the mixture from step (g) into its organic and aqueous phases;

(i) washing the organic phase from step (h) first with water and then with a concentrated, aqueous sodium chloride solution;

(j) drying the solution from step (i) over anhydrous sodium sulfate;

(k) combining the dried solution from step (j) with MEHQ (l) concentrating the solution from step (k) in vacuo to give the desired product.

The (meth)acrylated polyester diols of the present invention are also expected to be useful in applications other than dental composites, particularly in coating systems, for example, for coating metals, for industrial finishes, wood finishes, and for coating hard plastics.

Dental Composite Materials

The present invention further provides an uncured dental composite material comprising:

(a) at least one compound of Formula I (b) optionally at least one other polymerizable (meth) acrylic ester;

(c) at least one polymerization initiator compound; and (d) at least one filler.

Other Polymerizable (meth)acrylic Ester Component

Examples of suitable materials for the polymerizable (meth)acrylic ester component include but are not limited to 2,2'-bis[4-(2-hydroxy-3-methacryloyloxypropyl)phenyl]propane ("Bis-GMA"); ethoxylated Bisphenol A dimethacrylate ("EBPDMA"); 1,6-bis-[2-methacryloyloxy-ethoxycarbonylamino]-2,4,4-trimethylhexane ("UDMA"); 1,1,1-tri[4-2-methyl-2-methacryloxyethoxy)-phenyl]ethane ("THPE PO MA"); and butanedioic acid, ethylidynetris[4,1phenyleneoxy(2-hydroxy-3,1-propanediyltris[2-[[(2-methyl-1-oxo-2-propenyl)oxy]ethyl] ester. ("THPE GE Su-HEMA").

A preferred additional polymerizable (meth)acrylic ester component according to the present invention comprises a compound of Formula II as follows:

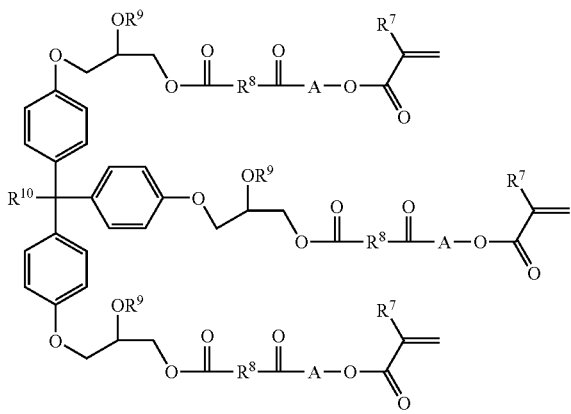

II wherein:
each $R^7$ is independently hydrogen or methyl;
each $R^8$ is an alkylene having 2 to 14 carbon atoms, or an alkenylene having 2 to 8 carbon atoms, or a divalent alicyclic hydrocarbon having 5 to 14 carbon atoms, or a phenylene, which is optionally substituted with halogen or an alkyl group having 1 to 5 carbon atoms;
each $R^9$ is independently selected from hydrogen, acetyl, methyl, ethyl, $C_{3-6}$ linear or branched alkyl, or benzyl;
$R^{10}$ is independently selected from hydrogen, methyl, ethyl, $C_{3-6}$ linear or branched alkyl, phenyl, or benzyl; and
each A is a repeating unit of the formula:

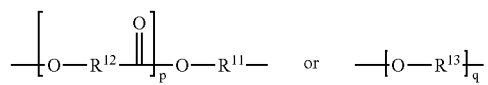

wherein:
each $R^{11}$ is independently an alkylene having 2 or 3 carbon atoms,
each $R^{12}$ is independently an alkylene having 2 to 7 carbon atoms,
each $R^{13}$ is independently an alkylene having 2 to 5 carbon atoms,
p is an integer of 1 to 10,
and q is an integer of 1 to 10.

A particularly preferred compound of Formula II is butanedioic acid, ethylidynetris[4,1 phenyleneoxy(2-hydroxy-3,1-propanediyltris[2-[[(2-methyl-1-oxo-2-propenyl)oxy]ethyl] ester ("THPE GE Su-HEMA"):

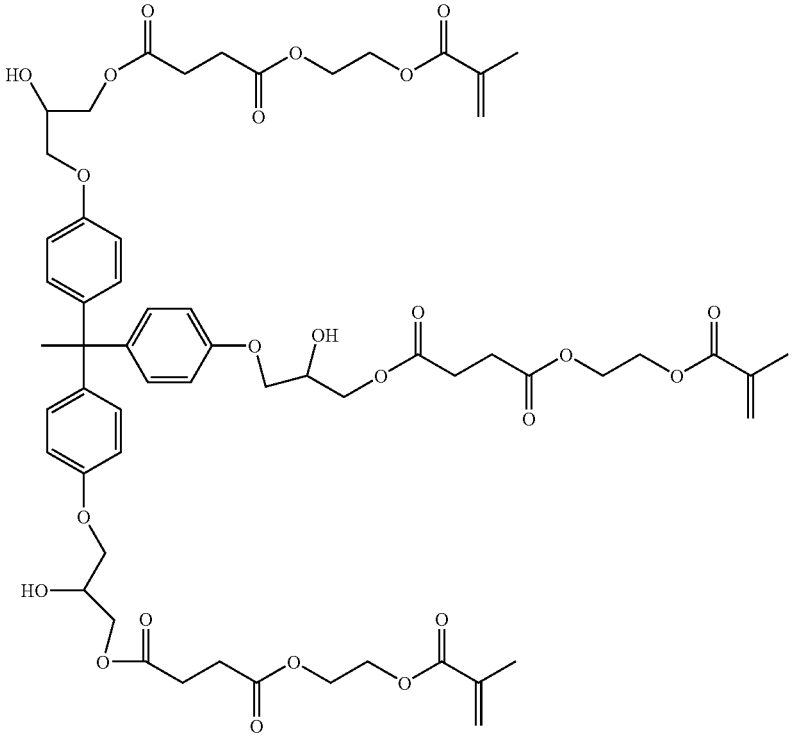

One method of preparing the compound of Formula II is the following:

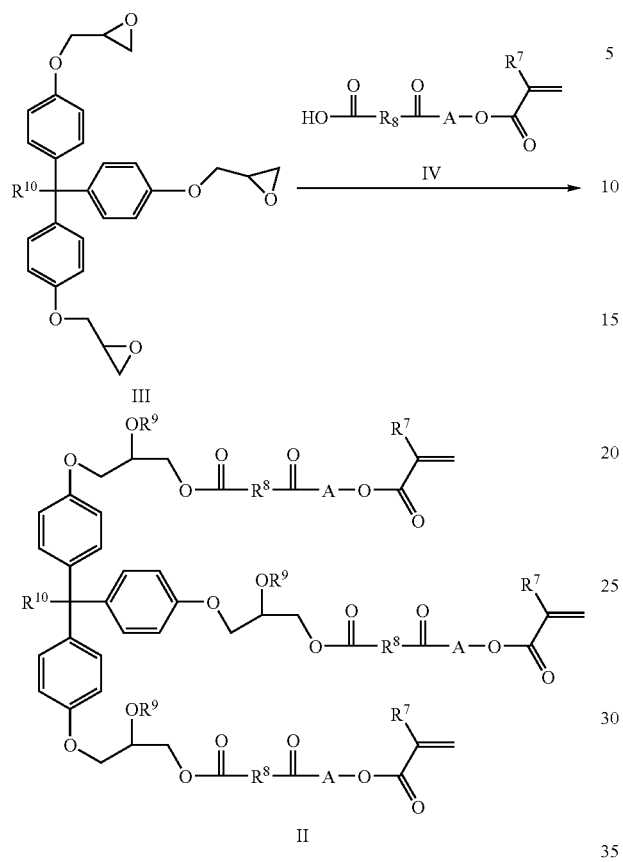

Triepoxides of Formula III are commercially available. For example, compound II where $R^{10}$=methyl (i.e., 1,1,1-tris(p-hydroxyphenylethane) triglycidyl ether), is available from E.I. du Pont de Nemours & Co., Inc. (Wilmington, Del.) under the trade name THPE-GE. Other compounds of Formula III (where $R^{10}$ is defined as above) can be prepared by the scheme below.

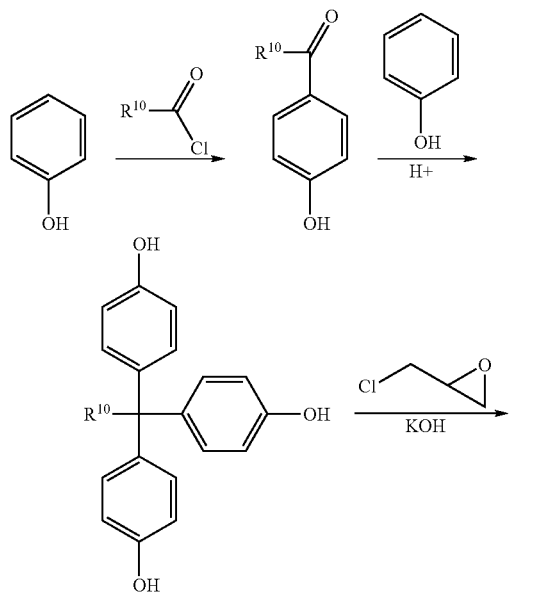

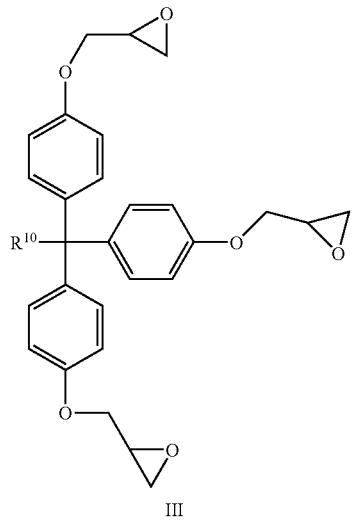

A compound of Formula III is treated with at least three moles of the carboxy methacrylate compound of Formula IV. The carboxylic acid of Formula IV opens the epoxide rings in Formula III to give the desired product. The reaction gives the hydroxy compound ($R^9$=H). The hydroxy compound can be further alkylated or acylated by any means known in the art. For example, it can be treated with acetic anhydride to give the acetylated product ($R^9$=—C(O)CH$_3$).

Suitable carboxy methacrylate compounds can be prepared by treatment of, for example, hydroxyethyl (meth)acrylate or hydroxypropyl (meth)acrylate with a cyclic anhydride to give the corresponding carboxy methacrylate compound. Preferred anhydrides include succinic anyhydride, maleic anhydride, and phthalic anhydride. Other suitable anhydrides include, those containing an anhydride function as part of a five or six member ring.

Some examples of syntheses and structures of carboxy methacrylates (IVA, IVB, IVC) are shown below.

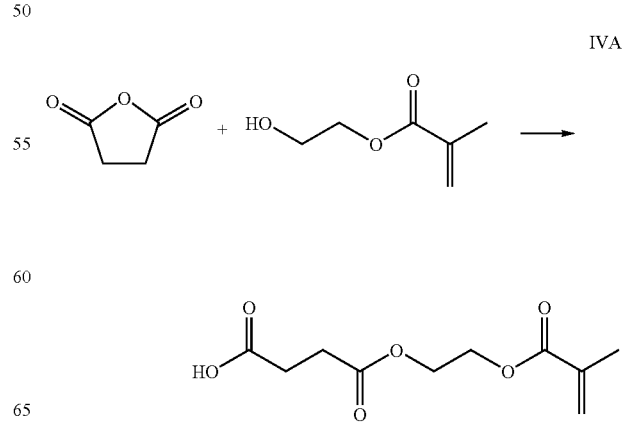

Other suitable carboxy methacrylates are described in U.S. Pat. No. 4,883,899, Col 2, line 37 to Col 3, line 17. There, hydroxyethyl methacrylate is used as an initiator for the ring opening polymerization of caprolactone. The resulting hydroxy methacrylates are commercially available from Daicel Chemical Industries, Ltd. (Tokyo, Japan) under the trade name Placcel. For example, Placcel FM 3 is the addition product of hydroxyethyl methacrylate with three moles of caprolactone. These products can be reacted with cyclic anhydrides to give carboxy functional methacrylates useful in the present invention.

Catalysts for the reaction may include any known in the art for the reaction of carboxylic acids with epoxides. They may include nitrogen-containing compounds such as triethylamine, imidazole, 2-methyl imidazole, N,N-dimethyl benzyl amine, pyridine, and the like. They may include Lewis acids such as zinc acetate or zinc stearate.

These compounds can be purified by any method indicated to one skilled in the art. Typical purification procedures might include extraction, distillation, crystallization and preparative chromatography.

In a preferred uncured dental composite, the compounds of Formula I and Formula II are used in a weight ratio of ranging from about 1:99 to 25:75. At this weight ratio, the viscosity of the uncured dental composite is low enough to allow fillers to be added and adequately mixed. The resulting material, when cured, shows relatively low shrinkage with good mechanical properties.

Another compound that may be used in addition to, or in place of, a compound of Formula II is a compound of Formula V.

wherein $R^7$, A, $R^8$, $R^9$, are as defined in relation to the compound of Formula II, and each $R^{14}$ is independently selected from the group consisting of hydrogen, methyl, ethyl, $C_{3-6}$ linear or branched alkyl, phenyl, benzyl, and the two $R^{14}$ groups may be taken together to form a substituted or unsubstituted cyclic aliphatic ring having 5 or 6 carbons in the ring, including the carbon to which both $R^{14}$ groups are attached.

A preferred compound of Formula V is shown below.

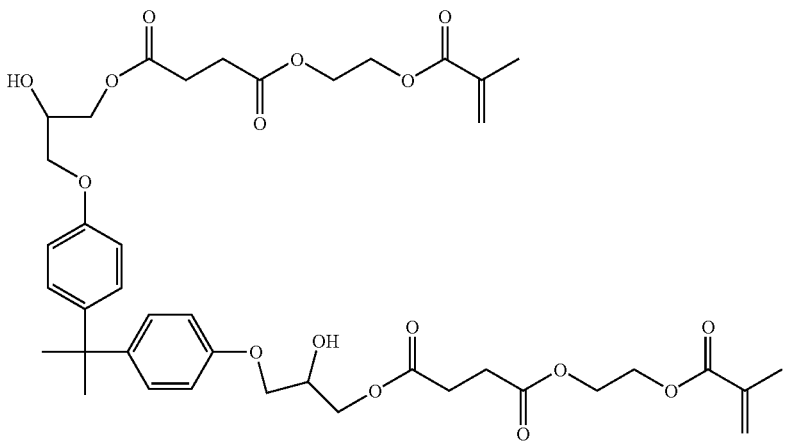

Such compounds may be synthesized as shown below.

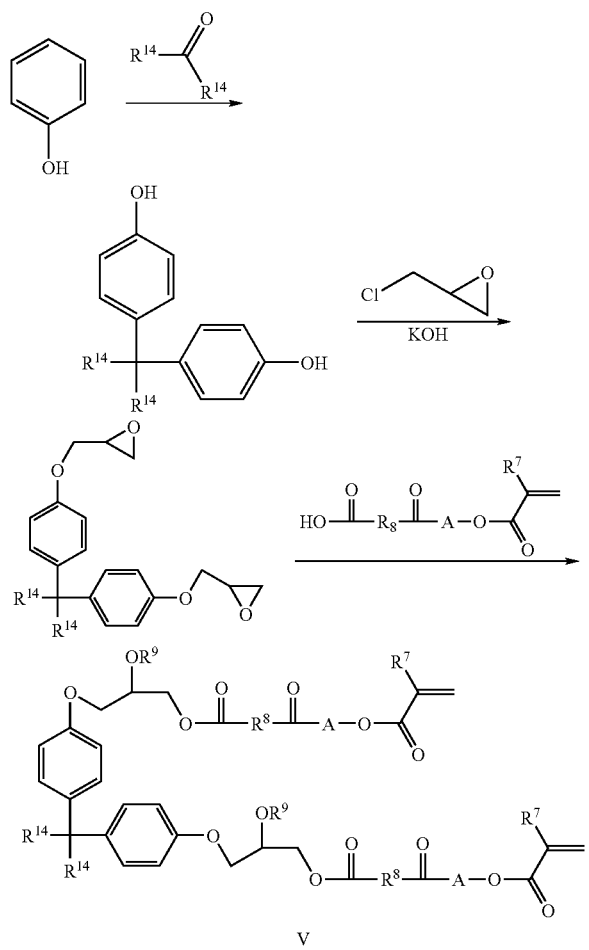

Some of the compounds of Formula V have been described in, for example, U.S. Pat. No. 3,367,992 Col. 6, line 27 to Col. 7, line 21, although not in relation to use in dental composites.

The polymerizable (meth)acrylic ester component may include additional polymerizable (meth)acrylic ester compounds. These additional polymerizable (meth)acrylic ester compounds may include both monofunctional compounds and polyfunctional compounds, where "monofunctional" denotes a compound having one (meth)acrylic group and "polyfunctional" denotes a compound having more than one (meth)acrylic ester group.

Other examples of polyfunctional (meth)acrylic ester compounds include, without limitation, Bis-GMA, EBPDMA, UDMA, and other urethane di(meth)acrylates.

Polymerization Initiator Compounds

Suitable polymerization initiator compounds include peroxy-type initiators such as benzoyl peroxide, dicumyl peroxide, lauryl peroxide, tributyl hydroperoxide, and other materials familiar to those skilled in the art. Azo-type initiators such as 2,2'-azobis(isobutyronitrile), 2,2'-azobis(2,4-dimethyl valeronitrile), 2,2'-azobis(2-methyl butane nitrile), and 4,4'-azobis(4-cyanovaleric acid) may also be used.

A preferred initiator system is the photosensitizer camphorquinone, used in conjunction with a tertiary amine like ethyl dimethylaminobenzoate or dimethylaminoethyl methacrylate.

The polymerization initiator (optionally with a photosensitizer) can be used in the range of about 0.1 weight percent to about 5 weight percent, preferably about 0.2 weight percent to about 3 weight percent, and more preferably about 0.2 weight percent to about 2 weight percent. The percentages are based on the total weight of the uncured dental composite, exclusive of filler.

Fillers

One class of fillers that may be used in the uncured dental composites of the present invention is inorganic fillers. Among the preferred inorganic fillers are barium aluminum silicate, barium aluminum borosilicate, ytterbium trifluoride, glass beads, silica, quartz, borosilicates, alumina, and alumina silicates, Mixtures of inorganic fillers may also be employed. The mean particle size of the inorganic fillers is preferably between about 0.5 and 15 μm.

Another class of fillers that may be used in the uncured dental composites of the present invention is organic fillers. Suitable organic fillers include prepolymerized fillers ("prepolymerized" in the sense that organic monomers have been polymerized to produce an organic resin, which, optionally, can be ground, prior to their inclusion in the uncured dental composites of this invention). Such prepolymerized fillers may be included in the uncured dental composites of the invention alone or in combination with an inorganic filler. These prepolymerized fillers can also optionally contain inorganic fillers such as those described above.

The total amount of filler in the uncured dental composites of the present invention can range from about 20 weight percent to about 90 weight percent, preferably from about 40 weight percent to about 90 weight percent, and more preferably from about 50 weight percent to about 85 weight percent. The percentages are based on the total weight of the uncured dental composite.

Additional Optional Ingredients

In addition to the components described above, the composite material may contain additional, optional ingredients. These may comprise activators, pigments, radiopaquing agents, stabilizers, antioxidants, and other materials.

The uncured dental composite material of the present invention can be prepared using any mixing means known in the art. Such methods include, but are not limited to, roll mills, vibratory mixers, sigma mixers, planetary mixers, SpeedMixers™ (from Flack Tek, Inc., Landrum, S.C.), extruders, Buss Kneaders (Coperion Holding GmbH, Stuttgart, Germany), and Brabender Plasticorders® (Intellitorque, Brabender, Hackensack, N.J.

The dental composite materials of the present invention can be used to fill cavities in teeth. Other treatments may include preventative, restorative, or cosmetic procedures in teeth. Typically, without limiting the method to a specific order of steps, the dental composite materials are placed on dental tissue, either natural or synthetic, cured, and shaped as necessary to conform to the target dental tissue. Dental tissue includes, but is not limited to, enamel, dentin, cementum, pulp, bone, and gingiva.

The dental composite materials may also be useful as dental adhesives, primers, bonding agents, pit and fissure sealants, cements, denture base and denture reline materials, orthodontic splint materials, and adhesives for orthodontic appliances. The materials also may be useful for making bridges, crowns, inlays, onlays, laminate veneers, and facings. The materials of the invention also may be useful for prosthetic replacement or repair of various hard body structures such as bone and also may be useful for reconstructive purposes during surgery, especially oral surgery.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

Abbreviations

The meaning of abbreviations is as follows: "hr" means hour(s), "min" means minute(s), "mL" means milliliter(s), "m" means meter, "cm" means centimeter(s), "mm" means millimeter(s), "em" means micrometer(s), "nm" means nanometer(s), "g" means gram(s), "mol" means mole(s), "mmol" means millimoles, "N" means Newton(s), "rpm" means revolutions per minute, "wt %" means weight percent (age), "mW" means milliwatt(s), "Mw" means weight average molecular weight, "MPa" means megaPascal(s), "MHz" means megaHertz, "std dev" means standard deviation, "avg dev" means average deviation, "d50" means 50% of particles have a diameter below a given size, "EtOAc" means ethyl acetate, "MEHQ" means 4-methoxyphenol, "PTFE" means polytetrafluoroethylene, "TH F" means tetrahydrofuran, "NMR" means nuclear magnetic resonance (spectroscopy), "IR" means infrared (spectroscopy), "ATR" means attenuated total reflectance, "DSC" means differential scanning calorimetry, "GPC" means gel permeation chromatography, "THPE GE" means 1,1,1-tris(p-hydroxyphenyl) ethane triglycidyl ether, "Bis-GMA" means bisphenol-A-glycidyl methacrylate, "TEGDMA" means triethylene glycol dimethacrylate, and "EDB" means ethyl 4-dimethylaminobenzoate.

Materials 1,1,1-tris(p-hydroxyphenyl) ethane triglycidyl ether ("THPE GE") was obtained from E. I. du Pont de Nemours & Co., Inc. (Wilmington, Del.). Caprolactone was obtained from Dow Chemical Company (Midland, Mich.). Mono-2-(methacryloyloxy)ethyl succinate, methacrylic anhydride (Aldrich catalog # 276685, stabilized with 2000 ppm of 2,4-dimethyl-6-tert-butyl phenol), and MEHQ were obtained from Aldrich Chemical Company (Milwaukee, Wis.). 1,4-cyclohexanedimethanol (CAS #105-08-8, Eastman product code # CHDM-D) was obtained from Eastman Chemical Company (Kingsport, Tenn.), Bisphenol-A-glycidyl methacrylate adduct ("Bis-GMA") was obtained from EssTech (Essington, Pa.), product code X 950-0000. Triethylene glycol dimethacrylate ("TEGDMA") was obtained from EssTech (Essington, Pa.), product code product code X 943-7424, inhibited with hydroquinone (50-70 ppm). Photosensitizers were obtained from Aldrich Chemical Company (Milwaukee, Wis.): camphorquinone (97%, catalogue #12, 489-3) and ethyl 4-dimethylaminobenzoate (99+%, catalogue #E2, 490-5). Aerosil® OX-50 fumed silica was obtained from Degussa (Dusseldorf, Germany). Schott 8235 UF1.5 glass powder was obtained from Schott AG (Mainz, Germany); it had a mean diameter, d50, of 1.5 μm and was treated with $C_{10}H_{20}O_5Si$ to a level of 2.3 wt % silane.

Sample Preparation

Uncured compositions intended for testing were packed into a stainless steel 2mm thick mold with at least one 2 mm×25 mm opening to enable two sides of the uncured composition to be exposed. The packed mold was sandwiched on either side with a polyester film, followed a glass plate. Bars of the uncured compositions were cured for the length of time per side and light intensities specified.

Analytical Methods

Molecular weight was determined by gel permeation chromatography (GPC) in THF using polystyrene standards.

The degree of monomer polymerization ("conversion") was measured by Fourier Transform Infrared (FTIR) spectroscopy, using the total attenuated reflectance (ATR) method. The absorbances of the IR peaks at 1610 $cm^{-1}$ (corresponding to aromatic C=C stretch) and 1640 $cm^{-1}$ (corresponding to methacrylate C=C stretch) were measured before and after irradiation. The peak absorbances were all normalized using appropriate baselines, and a % C=C value and a DC value were calculated according to the equations below, using normalized absorbance values:

$$\%C=C=[(A_{1640}/A_{1610})\text{after}/(A_{1640}/A_{1610})\text{before}] \times 100$$

$$DC \text{ (degree of conversion)} = 100 - \%C=C$$

The DC is referred to as the "C-Peak" degree of conversion.

The so-called "E-Peak" degree of conversion was also measured as described in *Dental Materials* (1990), 6(4), 241-249. This alternative method uses the ratio of the 1640 $cm^{-1}$ and the 1580 $cm^{-1}$ peaks, rather than the 1640 $cm^{-1}$ and 1610 $cm^{-1}$ peaks. The baseline of the 1640 $cm^{-1}$ peak is defined by drawing a baseline from the value at 1660 $cm^{-1}$ to the value at about 1590 $cm^{-1}$.

Fracture toughness ($K_{IC}$), flexural strength (ISO 4049), and density were determined on (2 mm×2 mm×25 mm) bars that were molded using the stainless steel mold described above. The molded bars were cured in the mold by irradiating each exposed side for 1 minute using either a) an array of three Spectrum® 800 dental lamps (DENTSPLY International, York, Pa.), each bearing an 8-mm light tip, at 550 mW/$cm^2$, or b) a Fusion UV Systems Inc.® (Gaithersburg, Md.) curing unit equipped with a Q-bulb (designed for emitting light at a wavelength suitable for camphorquinone excitation).

The metal mold was covered on both sides with a 3-mil (76-micron) polyester film to exclude oxygen.

Five bars were used for each of the fracture toughness and flexural strength tests. The bars were stored in glass vials until use and conditioned in water for 24 hr at 37° C., just prior to the tests.

The fracture toughness test was based on both the ASTM polymers standard (ASTM D5045) and the ASTM ceramics standard (ASTM C1421, precracked beam method). Testing was conducted at a test speed of 0.5 mm/min at room temperature and ambient humidity using a three-point bend fixture (span to depth ratio of 10). The specimens were molded using the flex bar mold specified in ISO 4049. The specimens were precracked halfway through their depth. Two modifications to the test procedures were made. The first was the use of smaller test specimens than those recommended in the ASTM C1421 standard (2 mm×2 mm×25 mm instead of the recommended minimum dimensions of 3 mm×4 mm×20 mm). The second was the use of a slitting circular knife to machine the precracks. The knife was 0.31 mm in thickness with a 9° single bevel. The modified test procedures produced precracks that were equivalent to precracks produced using the techniques recommended in ASTM D5045.

The percent shrinkage (% S) was determined by measuring the densities of uncured dental composites and of cured dental composites. The volumes were measured with an AccuPyc 1330 Pycnometer for 1-cm$^3$ Samples (Micromeritics Instrument Corporation, Norcross, Ga.), using argon. The density of the uncured dental composites was determined by measuring the volume of a known weight of composite (measured by an analytical balance with a resolution of ±0.0001 g). Briefly, the pycnometer was set up for 5 purges and 3 volume measurements per sample. The volume of a glass cup (about 0.36 cubic centimeters) and, then, the cup containing uncured composite (about 0.3 to 1 g) were measured sequentially. The volume of the uncured dental composite was calculated by subtracting the volume of the glass cup from the total volume of the cup with the uncured dental composite. The density of uncured composite $\rho_{uncured}$ is defined as grams of uncured composite divided by volume of uncured composite in cubic centimeters. The uncured paste was then pressed thin between two sheets of Mylar® polyester film and cured in a Triad® 2000™ Visible Light Curing Unit (DENTSPLY International) for two minutes on each side. The cured film was peeled from the Mylar® and ground to a coarse particulate with a mortar and pestle. The density of the cured dental composite was calculated in a manner similar to that of uncured composite as described above. The density of cured composite $\rho_{cured}$ is defined as grams of cured composite divided by volume of cured composite in cubic centimeters.

The percent shrinkage (% S) was calculated from the formula, $$[(\rho_{cured} - \rho_{uncured})/(\rho_{cured})] \times 100 = \% \, S.$$

EXAMPLE 1

Preparation and Purification of THPE GE Su HEMA

A 1 L three neck flask equipped with a mechanical stirrer, condenser, thermocouple, and addition funnel was charged with THPE GE (112.5 g), mono-2-(methacryloyloxy)ethyl succinate (218.3 g), triethylamine (1.2 g), and Prostab® 5415 (0.2 g,). The mixture was heated to 80° C. for 7.5 hr to obtain a pale yellow mixture. The mixture was dissolved in 1250 mL of ethyl acetate, extracted with 500 mL of water followed by 500 mL of saturated sodium bicarbonate solution. The solution was dried with anhydrous sodium sulphate, then added to 1 liter of silica gel (Merck silica gel 60), and the solvent was removed. The silica gel containing the compound was then added to a column with 2500 g of silica gel and was eluted with a mixture of hexanes and ethyl acetate to isolate a purified fraction of the desired compound, THPE GE Su HEMA. $^1$H NMR (500 MHz, CDCl$_3$) δ 1.93 (s, 9H), 2.08 (s, 3H), 2.61-2.7 (m, 12H), 3.8-4.2 (m, 15H), 4.3-4.4 (m, 12H), 5.6 (m, 3H), 6.1 (m, 3H), 6.75 (m, 6H), 6.98 (m, 6H).

EXAMPLE 2

Preparation of dimethacrylated ε-caprolactone-1,4-cyclohexanedimethanol adduct ("DM-CL-CHDM")

An adduct was made by heating three moles of caprolactone with one mole of 1,4-cyclohexanedimethanol at 140° C. for four hours with 0.01 wt. percent of dibutyltin dilaurate and 0.1 wt. percent of xylene. The material was then cooled to 80° C. and purified by filtration through a sparkler filter.

A solution of the ε-caprolactone-1,4-cyclohexanedimethanol adduct (average Mw=487; 194 g, 398 mmol, 797 mmol reactive OH), methacrylic anhydride containing 2000 ppm of Topanol A (140 g, 908 mmol) and sodium acetate (1.40 g, 17.1 mmol) was heated to 75-80° C. for 6 hr under a constant flow of dry air. After cooling to room temperature, the resulting product mixture was stirred with 5% aqueous sodium carbonate (500 mL) for 1 hr. The mixture was then treated with ethyl ether (300 mL) and stirred gently overnight. The mixture was allowed to separate into organic and aqueous fractions and the aqueous fraction was discarded. The organic (ether) fraction was washed first with 5% aqueous sodium carbonate (2×300 mL), then with water (6×200 mL) and finally with brine (concentrated, aqueous sodium chloride solution) (100 mL). The ether solution was dried over anhydrous sodium carbonate and then treated with MEHQ (0.050 g). The resulting solution was concentrated in vacuo with mild heating to give a clear oil. The oil, maintained at room temperature, was further concentrated by first applying a reduced vacuum (ca. 20 torr, with filtered air-bleed) for 4 hr, followed by high vacuum for 3 hr, ultimately furnishing 210 gm of the product.

IR spectroscopy of the neat product showed an absence of OH stretching between 3450 and 3550 cm$^{-1}$. Additionally, a strong ester peak centered near 1732 cm$^{-1}$ and a peak at 1637 cm$^{-1}$ representing the methacrylate double bond were noted in the IR spectrum. $^1$H NMR spectroscopy (in CDCl$_3$) confirmed the presence of terminal methacrylate groups in the product, with vinylic proton resonances near 5.5 (1H) and 6.1 ppm (1H).

EXAMPLES 3, 4, and 5

Dental Composite Materials made with THPE-GE Su HEMA and 2 to 10 wt % DM-CL-CHDM Dental composite materials were made using a first monomer component, the purified THPE GE Su HEMA from Example 1, and a second monomer component, the dimethacrylated ε-caprolactone-1,4-cyclohexanedimethanol adduct from Example 2. Photoinitiators used were camphorquinone and EDB. Fillers used were Schott 8235 glass and Degussa Aerosil® OX-50.

The monomer components, photoinitiators, and fillers were combined, in the amounts noted in Table 1, in the "max 40" size cup of a Flack Tek SpeedMixer™ under yellow light to avoid premature polymerization. The contents were mixed for two 30-second intervals at 3500 rpm. The mixture was wrapped in foil to exclude light and transferred to a Sigma mixer ("B&P Model 2 cubic inch Horizontal Batch Mixer", B&P Process Equipment and Systems LLC, 1000 Hess Ave., Saginaw, Mich., USA) preheated to 45° C. The sample was mixed under yellow light for 15 minutes at 10 rpm at atmospheric pressure, 15 minutes at 20 rpm at atmospheric pressure, and 30 minutes at 15 rpm under a vacuum of 210 torr. Any buildup of paste above the mixer blades was pushed material down into the main part of the mixture, with a spatula between each of the steps. The resulting paste was stored in a foil-wrapped container to exclude light and refrigerated until use, to prevent premature curing.

The paste was formed into bars, cured, and tested as described above. Results are presented in Table 1.

TABLE 1

|  | Ex. 3 | Ex. 4 | Ex. 5 |
|---|---|---|---|
| First Component |  |  |  |
| THPE GE Su HEMA (g) | 9.0 | 9.5 | 9.8 |
| Second Component |  |  |  |
| Dimethacrylated ε-caprolactone-1,4-cyclohexanedimethanol adduct (g) | 1.0 | 0.5 | 0.2 |
| Initiators and Fillers |  |  |  |
| Camphorquinone (g) | 0.132 | 0.132 | 0.132 |
| EDB (g) | 0.132 | 0.132 | 0.132 |
| Schott 8235 glass powder (g) | 28.0 | 28.0 | 28.0 |
| Degussa Aerosil ® OX-50 fumed silica (g) | 2.0 | 2.0 | 2.0 |
| Properties |  |  |  |
| Conversion %, C-peak | 82% | 90% | 87% |
| Shrinkage (ground film-Ar) %, average of 2 | 1.64% | 1.53% | 1.43% |
| Shrinkage Stress (N) | 50 | 49 | 51 |
| std dev | 4 | 1 | 3 |
| Flex Strength (MPa) | 114 | 116 | 109 |
| std dev | 19 | 21 | 12 |
| Fracture Toughness [MPa (m$^{0.5}$)] | 2.07 | 2.22 | 2.38 |
| std dev | 0.07 | 0.16 | 0.15 |

EXAMPLES 6, 7, and 8

Shrinkage of Bis-GMA/DM-CL-CHDM Composites vs Bis-GMA/TEGDMA Composites

Bisphenol-A-glycidyl methacrylate adduct ("Bis-GMA") was obtained from EssTech (Essington, Pa.), product code X 950-0000. Triethylene glycol dimethacrylate ("TEGDMA") was obtained from EssTech (Essington, Pa.), product code X 943-7424. DM-CL-CHDM was prepared in Example 2 above. The monomer components, photoinitiators, and fillers were combined in the "max 40" size cup of a Flack Tek SpeedMixer™ under yellow light to avoid premature polymerization. The contents were mixed for two 30-second intervals at 3500 rpm. The mixture was debubbled in the vacuum oven at 40° C. for 12 hrs. The resulting paste was stored in a foil-wrapped container to exclude light and stored in a desiccator before use.

The composition and shrinkage of the dental composites are shown in Table 2. The shrinkage measurement by ground-film Ar method was carried out as described above.

The results show that using DM-CL-CHDM to replace TEGDMA in the traditional dental composite materials significantly reduced the shrinkage. The shrinkage of the Bis-GMA DM-CL-CHDM composite materials decreased with reduced amount of DM-CL-CHDM.

TABLE 2

|  | Ex. 6 | Ex. 7 | Ex. 8 |
|---|---|---|---|
| Ratio of First Component to Second Component | 70:30 | 70:30 | 90:10 |
| First Component |  |  |  |
| Bis-GMA (g) | 3.5 | 3.5 | 4.5 |
| Second Component |  |  |  |
| TEGDMA (g) | 1.5 | 0 | 0 |
| DM-CL-CHDM (g) | 0 | 1.5 | 0.5 |
| Initiators and Fillers |  |  |  |
| Camphorquinone (g) | 0.065 | 0.065 | 0.065 |
| EDB (g) | 0.065 | 0.065 | 0.065 |
| Schott 8235 glass powder (g) | 14.0 | 14.0 | 14.0 |
| Degussa Aerosil ® OX-50 fumed silica (g) | 1.0 | 1.0 | 1.0 |
| Properties |  |  |  |
| Shrinkage (ground film-Ar) %, average of 2 | 3.26% | 2.57% | 2.27% |

This experiment demonstrates that DM-CL-CHDM allows for the creation of a composite with superior shrinkage performance relative to TEGDMA.

We claim:

1. An uncured dental composite material comprising:
   (i) a composition comprising at least one compound of the Formula I:

$$E^1\text{-}R^1{}_n\text{—O—}R^2\text{-Q-}R^3\text{—O—}R^4{}_m\text{-}E^2 \qquad I$$

wherein:
   Q is selected from the group consisting of:
   (a) a carbocyclic ring containing 5 or 6 carbon atoms with up to 3 $C_{1\text{-}3}$ alkyl substituents on the ring;
   (b) S—R$^5$-T wherein S and T are each independently carbocyclic rings containing 5 or 6 carbon atoms with up to 3 $C_{1\text{-}3}$ alkyl substituents on the ring, and R$^5$ is a covalent bond or an alkylene group containing 1, 2, 3 or 4 carbon atoms; and
   (c) a carbocyclic fused ring system containing two fused rings containing a total of 8 to 10 carbon atoms with up to 4 $C_{1\text{-}3}$ alkyl substituents on the fused ring system;
   R$^2$ and R$^3$ are each independently selected from the group consisting of a covalent bond and an alkylene group containing 1, 2, 3, or 4 carbon atoms;
   R$^1$ is a repeat unit of the formula

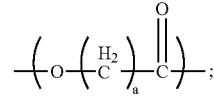

R$^4$ is a repeat unit of the formula

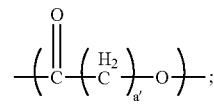

E$^1$ and E$^2$ are each independently

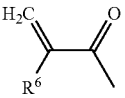

wherein R$^6$ is H (acryloyl) or CH$^3$ (methacryloyl); and
   n and m are each independently an integer greater than 0; provided that for each of the n groups of the formula

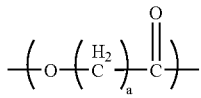

a is independently an integer from 3 to 6; and
provided that for each of the m groups of the formula

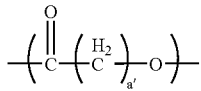

a' is independently an integer from 3 to 6; and
provided that neither $R^2$ nor $R^3$ is a covalent bond bonded directly to an aromatic ring; and
provided that the degree of polymerization of the at least one compound is between 2 and 30;
(ii) at least one compound of the Formula V

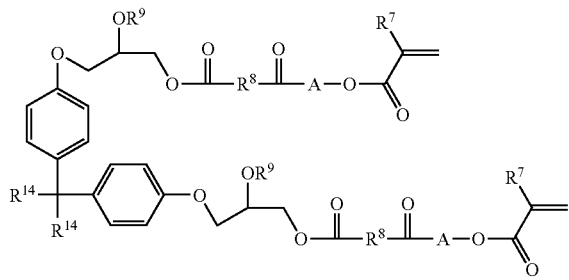

wherein
each $R^7$ is independently hydrogen or methyl;
each $R^8$ is an alkylene having 2 to 14 carbon atoms, or an alkenylene having 2 to 8 carbon atoms, or a divalent alicyclic hydrocarbon having 5 to 14 carbon atoms, or a phenylene, which is optionally substituted with halogen or an alkyl group having 1 to 5 carbon atoms;

each $R^9$ is independently selected from the group consisting of hydrogen, acetyl, methyl, ethyl, $C_{3-6}$ linear alkyl, $C_{3-6}$ branched alkyl, and benzyl;
each A is a repeating unit of the formula:

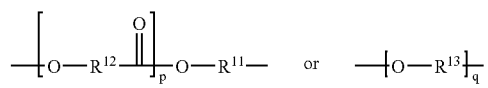

wherein:
each $R^{11}$ is independently an alkylene having 2 or 3 carbon atoms,
each $R^{12}$ is independently an alkylene having 2 to 7 carbon atoms,
each $R^{13}$ is independently an alkylene having 2 to 5 carbon atoms,
p is an integer of 1 to 10,
each $R^{14}$ is independently selected from the group consisting of hydrogen, methyl, ethyl, $C_{3-6}$ linear alkyl, $C_{3-6}$ branched alkyl, phenyl, and benzyl,
and the two $R^{14}$ groups may be taken together to form a substituted or unsubstituted cyclic aliphatic ring having 5 or 6 carbons in the ring, including the carbon to which both $R^{14}$ groups are attached;
(iii) at least one polymerization initiator compound; and
(iv) at least one filler.

2. The uncured dental composite material of claim 1, wherein Q is 1,4-cyclohexylene; $R^2$ and $R^3$ are each methylene, $a=a'=5, E^1=E^2$, and $R^6$ is methyl, and the degree of polymerization is between 2 and 6.

3. The uncured dental composite material of claim 1, wherein the compound of Formula V is:

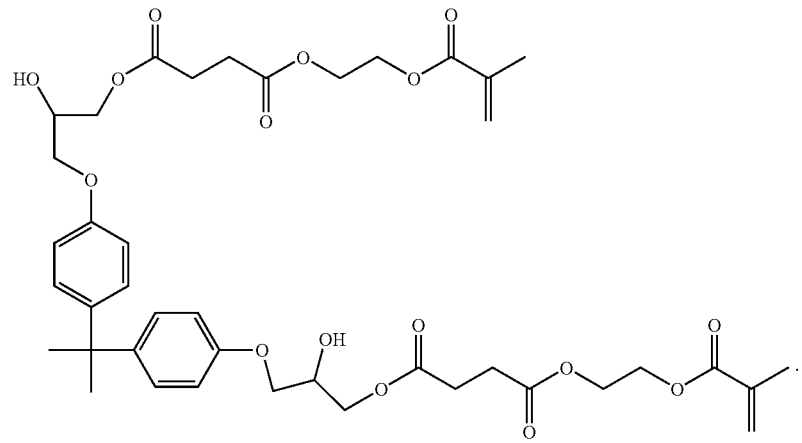

4. The uncured dental composite material of claim 1 further comprising at least one photoinitiating accelerator, an activator, a pigment, a radiopaquing agent, a stabilizer, and an antioxidant.

5. A dental restoration article that is made by forming and curing the uncured dental composite material of claim 1.

* * * * *